US010384235B2

(12) United States Patent
Aronson et al.

(10) Patent No.: US 10,384,235 B2
(45) Date of Patent: Aug. 20, 2019

(54) METHOD OF FACILITATING CHECK GRADER REACTION TO OUTPUT PRODUCED BY AUTOMATIC BOARD LUMBER GRADING SYSTEM

(71) Applicant: Lucidyne Technologies, Inc., Corvallis, OR (US)

(72) Inventors: Hayden Michael Aronson, Corvallis, OR (US); Ryan T. Shear, Corvallis, OR (US)

(73) Assignee: Lucidyne Technologies, Inc., Corvallis, OR (US)

( * ) Notice: Subject to any disclaimer, the term of this patent is extended or adjusted under 35 U.S.C. 154(b) by 59 days.

(21) Appl. No.: 15/678,951

(22) Filed: Aug. 16, 2017

(65) Prior Publication Data
US 2018/0085789 A1 Mar. 29, 2018

Related U.S. Application Data

(60) Provisional application No. 62/398,764, filed on Sep. 23, 2016.

(51) Int. Cl.
*B07C 5/14* (2006.01)
*B07C 5/342* (2006.01)
(Continued)

(52) U.S. Cl.
CPC ............... *B07C 5/14* (2013.01); *B07C 5/342* (2013.01); *G01N 21/8986* (2013.01); *G01N 33/46* (2013.01); *G05B 19/4183* (2013.01); *G05B 2219/31296* (2013.01); *G05B 2219/31311* (2013.01)

(58) Field of Classification Search
None
See application file for complete search history.

(56) References Cited

U.S. PATENT DOCUMENTS

| 4,158,766 A | 6/1979 | Sjödin |
| 4,541,722 A | 9/1985 | Jenks |

(Continued)

FOREIGN PATENT DOCUMENTS

| CA | 2800409 A1 | 7/2013 |
| WO | 199011488 A1 | 10/1990 |

*Primary Examiner* — Roy Y Yi
*Assistant Examiner* — Geoffrey T Evans
(74) *Attorney, Agent, or Firm* — Stoel Rives LLP (57) ABSTRACT

A method of improving board feature quality grading facilitates human check grader reaction to grading output. The method entails specifying, for application by an automatic grading system to the faces of boards passing through a scanning zone, a virtual grade expressed by a range of values that overlap values in two of successive standard rule-based grades representing higher and lower board feature qualities; producing a signal in response to detection of a board feature quality representing a virtual grade value of a board analyzed by the automatic grading system; indicating, in response to the signal, a virtual grading designation onto the board to alert a check grader to assess whether the board exhibits board feature quality that exceeds the lower board feature quality; and assigning to the board the standard rule-based grade representing the higher board feature quality whenever the check grader's assessment concurs with the virtual grade designation.

10 Claims, 10 Drawing Sheets

(51) Int. Cl.
*G01N 33/46* (2006.01)
*G01N 21/898* (2006.01)
*G05B 19/418* (2006.01)

(56) References Cited

U.S. PATENT DOCUMENTS

| | | |
|---|---|---|
| 4,972,154 A | 11/1990 | Bechtel et al. |
| 5,111,861 A | 5/1992 | Gore et al. |
| 5,257,101 A | 10/1993 | Lee |
| 5,412,220 A | 5/1995 | Moore |
| 6,031,567 A | 2/2000 | Johnson |
| 6,122,065 A | 9/2000 | Gauthier |
| 6,272,437 B1 | 8/2001 | Woods et al. |
| 6,741,724 B1 * | 5/2004 | Bruce .................. G06F 17/273 382/101 |
| 6,826,990 B2 | 12/2004 | Olsen |
| 7,004,329 B2 | 2/2006 | Magnan |
| 7,200,458 B2 | 4/2007 | Carman et al. |
| 7,426,422 B2 | 9/2008 | Carman et al. |
| 9,678,019 B2 * | 6/2017 | Paul .................. G01N 21/8914 |
| 2003/0009258 A1 | 1/2003 | Conry |
| 2003/0178586 A1 | 9/2003 | Hubert et al. |
| 2004/0246473 A1 | 12/2004 | Hermary et al. |
| 2005/0021280 A1 | 1/2005 | Woods et al. |
| 2010/0141754 A1 | 6/2010 | Hiraoka |
| 2011/0050872 A1 | 3/2011 | Harbert et al. |
| 2013/0176419 A1 | 7/2013 | Conry et al. |
| 2014/0104579 A1 | 4/2014 | Blomquist et al. |

\* cited by examiner

METHOD OF FACILITATING CHECK GRADER REACTION TO OUTPUT PRODUCED BY AUTOMATIC BOARD LUMBER GRADING SYSTEM

RELATED APPLICATION

This application claims benefit of U.S. Patent Application No. 62/398,764, filed Sep. 23, 2016.

COPYRIGHT NOTICE

© 2017 Lucidyne Technologies, Inc. A portion of the disclosure of this patent document contains material that is subject to copyright protection. The copyright owner has no objection to the facsimile reproduction by anyone of the patent document or the patent disclosure, as it appears in the Patent and Trademark Office patent file or records, but otherwise reserves all copyright rights whatsoever. 37 CFR § 1.71(d).

TECHNICAL FIELD

This disclosure relates to board lumber grading systems and, in particular, to a method of improving fidelity of board feature quality designations by facilitating human reaction to grading output of an automatic grading system included in a board lumber scanning system.

BACKGROUND INFORMATION

Lumber is graded by application of regional grading standards, for example, the American Lumber Standards, which are based on one or more of the structural integrity, shape, dimensions, and appearance of a board. These grades take into account the sizes and locations of defects, together with the slopes of grains, shapes, and dimensions, to predict one or more of the load-bearing capacities and acceptable appearance of the boards. (These attributes of the boards, together with grade and trim symbols, are hereafter referred to collectively as "board attribute information.")

Board grading designations represent board feature quality information produced after analysis of the boards, typically by an automatic grading system. The grading designations are developed from successive standard rule-based grades, each of which is expressed as a range of values. The standard rule-based grades represent the above-recited board structure and appearance metrics, and the ranges of values of successive standard rule-based grades represent different degrees of board feature qualities.

The growing number of automatic grading machines introduced to the forest products industry requires human check graders to inspect board lumber at increased speeds. The most common issue with either human or automatic grading of a board is lack of time allocated to make a decision. Some systems display grading system-produced board feature quality information on monitors near the inspection line. However, when a check grader has only a fraction of a second to read and process board grading designation information, flip the board, and again read and process board grading designation information, even the most skilled check graders lack an ability to perform a grade check task to the best of ability.

When presented with too much information, a check grader tends to make decisions that the check grader determines would afford the highest probability of success. If unable to consider all available data, the check grader may make the best decision with only part of the information, which most often results in an unacceptable assessment of board feature quality.

SUMMARY OF THE DISCLOSURE

A method of improving board feature quality grading facilitates human check grader reaction to grading output produced by an automatic grading system that is included in a board lumber scanning system. The board lumber scanning system scans faces of boards that pass through a scanning zone and projects onto the boards grading designations that represent board feature quality information produced after analysis of the boards by the automatic grading system. The grading designations are developed from successive standard rule-based grades representing board structure and appearance metrics. Each of the standard rule-based grades is expressed as a range of values, and the ranges of values of successive standard rule-based grades represent different degrees of board feature qualities.

The method entails specifying, for application by the automatic grading system to the faces of boards passing through the scanning zone, a virtual grade expressed by a range of values that overlap values in two of the successive standard rule-based grades representing higher and lower board feature qualities; producing a signal in response to detection of a board feature quality representing a virtual grade value of a board analyzed by the automatic grading system; indicating, in response to the signal, a virtual grading designation onto the board to which the virtual grade corresponds to alert a check grader to assess whether the board exhibits board feature quality that exceeds the lower board feature quality of the two successive standard rule-based grades; and assigning to the board the standard rule-based grade representing the higher board feature quality whenever the check grader's assessment concurs with the virtual grade designation.

Performing the method of virtual grade marking reduces above-grade errors, which result in setting board lumber at monetary values that are less than what the board lumber is worth, and below-grade errors, which result in setting board lumber monetary values that are greater than what the board lumber is worth.

Additional aspects and advantages will be apparent from the following detailed description of preferred embodiments, which proceeds with reference to the accompanying drawings.

BRIEF DESCRIPTION OF THE DRAWINGS

FIGS. 5-1, 5-2, 5-3, and 5-4 are images developed by sequential processing of a depth image signal output of the 3D depth camera shown in FIGS. 1A and 1B.

DETAILED DESCRIPTION OF PREFERRED EMBODIMENTS

Figure 1A:
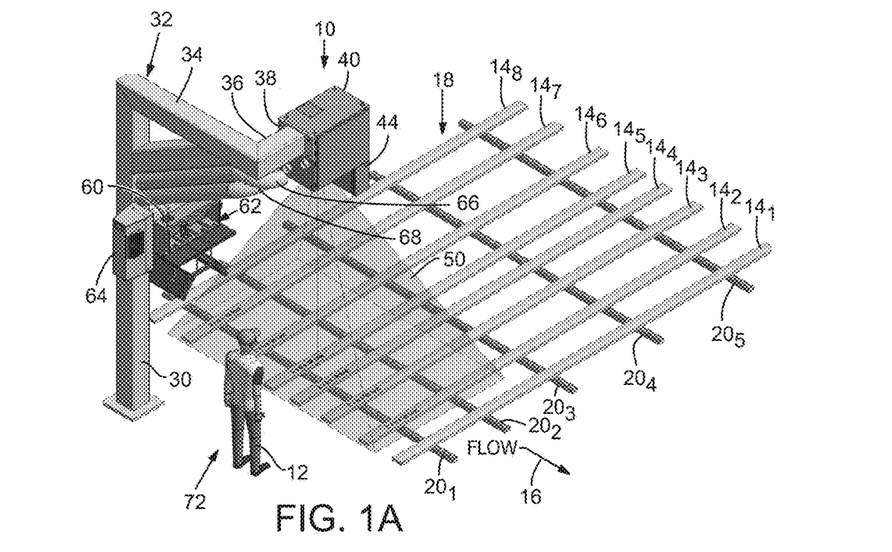
FIGS. 1A and 1B show from two different vantage points pictorial isometric views of a check grader-actuatable interface operating in a preferred embodiment in accordance with the present disclosure.
Figure 1B:
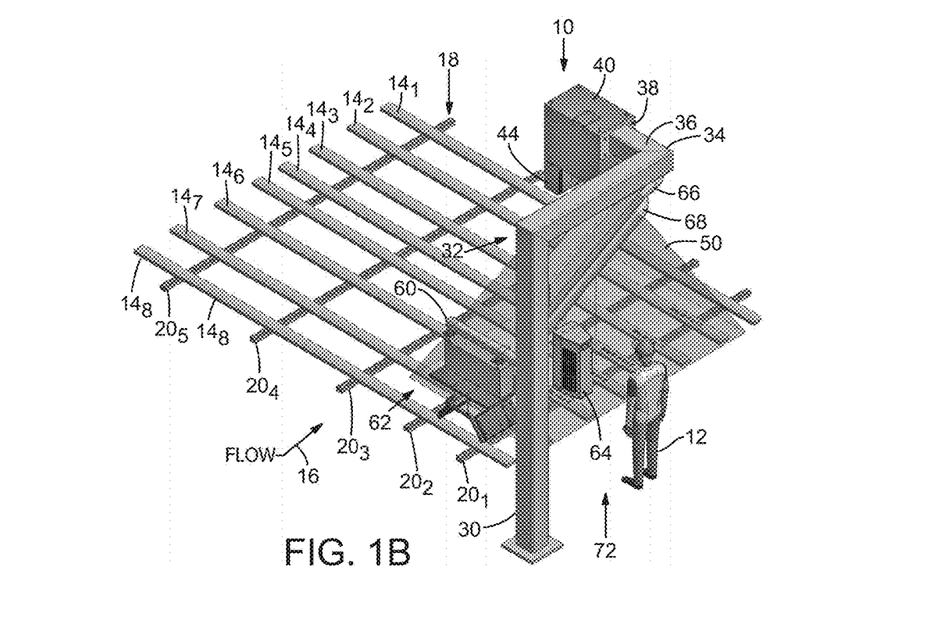

FIGS. 1A and 1B show from two different vantage points a check grader-actuatable interface 10 operating in a preferred embodiment in accordance with the present disclosure. With reference to FIGS. 1A and 1B, a check grader 12 inspects each one of eight grade-quality measured, generally parallel aligned boards $14_1$, $14_2$, $14_3$, $14_4$, $14_5$, $14_6$, $14_7$, and $14_8$ (collectively, "boards 14") transported along a board flow path 16 defined by a conveyor 18 formed of spaced-apart lug chains $20_1$, $20_2$, $20_3$, $20_4$, and $20_5$ (collectively, "lug chains 20"). Check grader 12 can be a human grader, quality control inspector, machine operator observing equipment operation, operation supervisor, or any other individual interested in system operation. Boards 14 are set in a generally perpendicular orientation relative to the lengths of lug chains 20 as they move boards 14 along board flow path 16. There are no lane dividers separating, or upwardly projecting lugs maintaining a uniform parallel alignment of, adjacent boards 16 transported by conveyor 18.

Figure 2A:
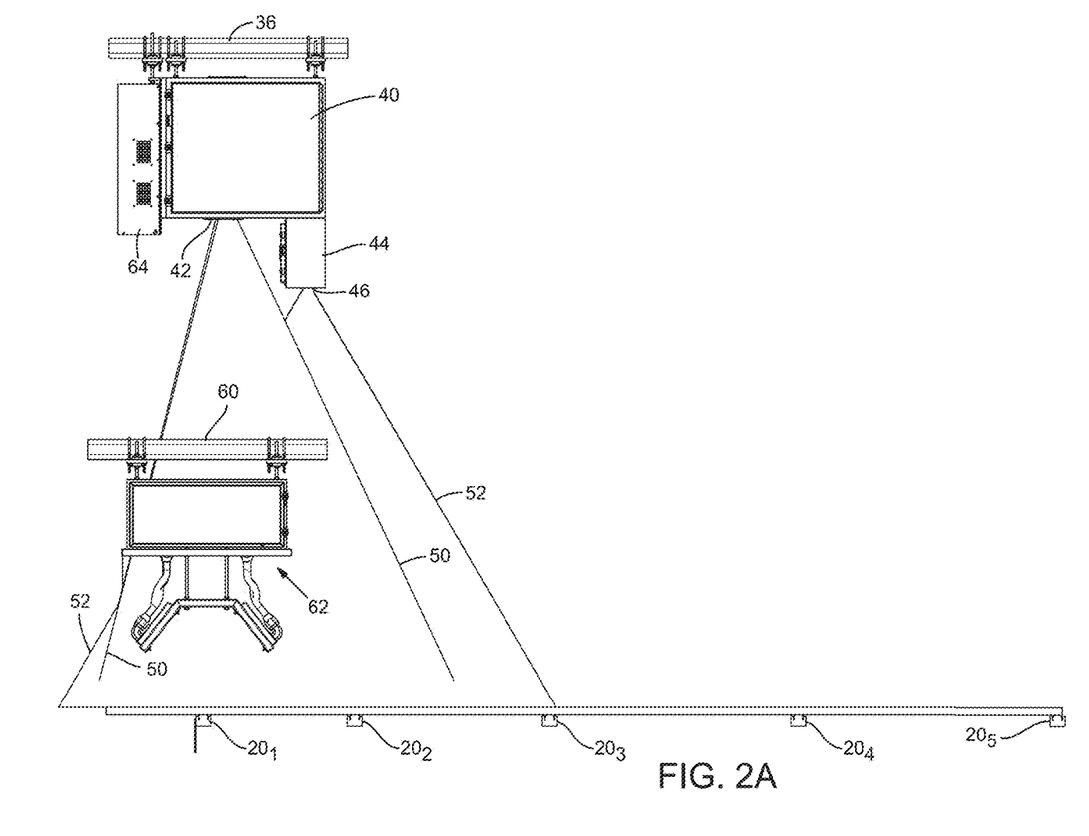
FIGS. 2A and 2B are diagrams showing in, respectively, the direction of a board flow path and the viewing direction of a check grader, the overlap of a field of view of an image projector and a field of view of a 3D depth camera shown in FIGS. 1A and 1B.
Figure 2B:
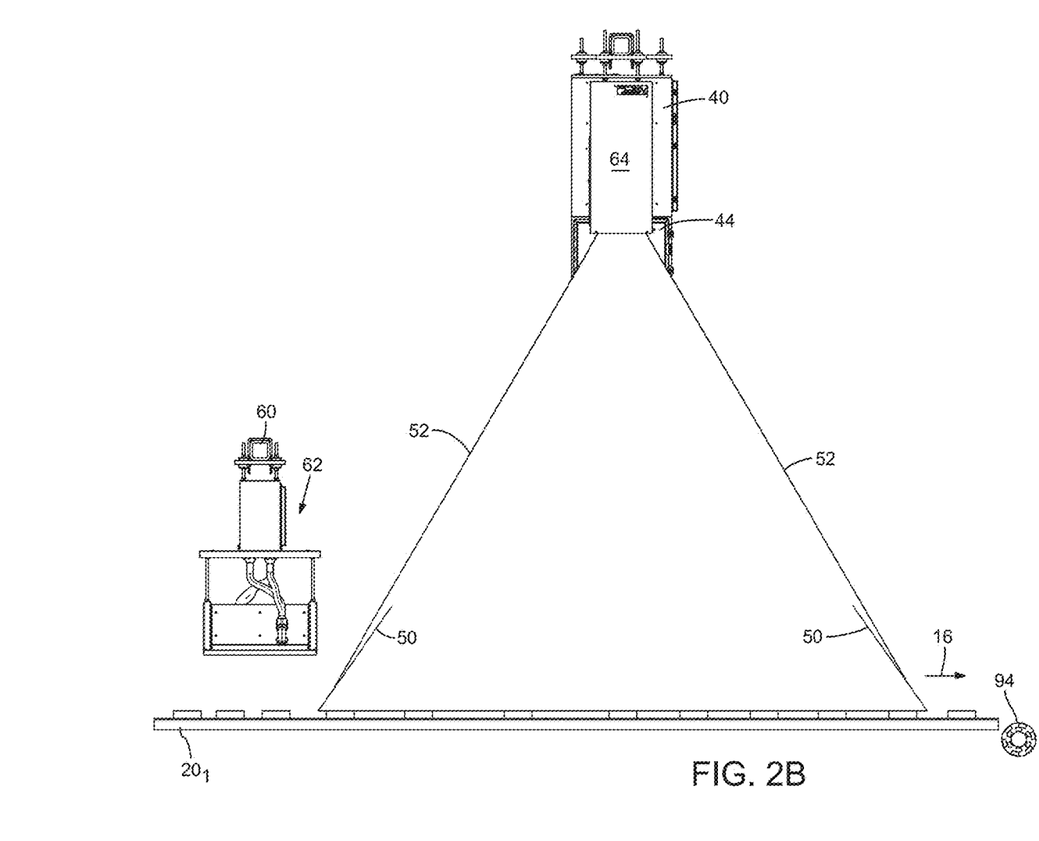
Figure 3:
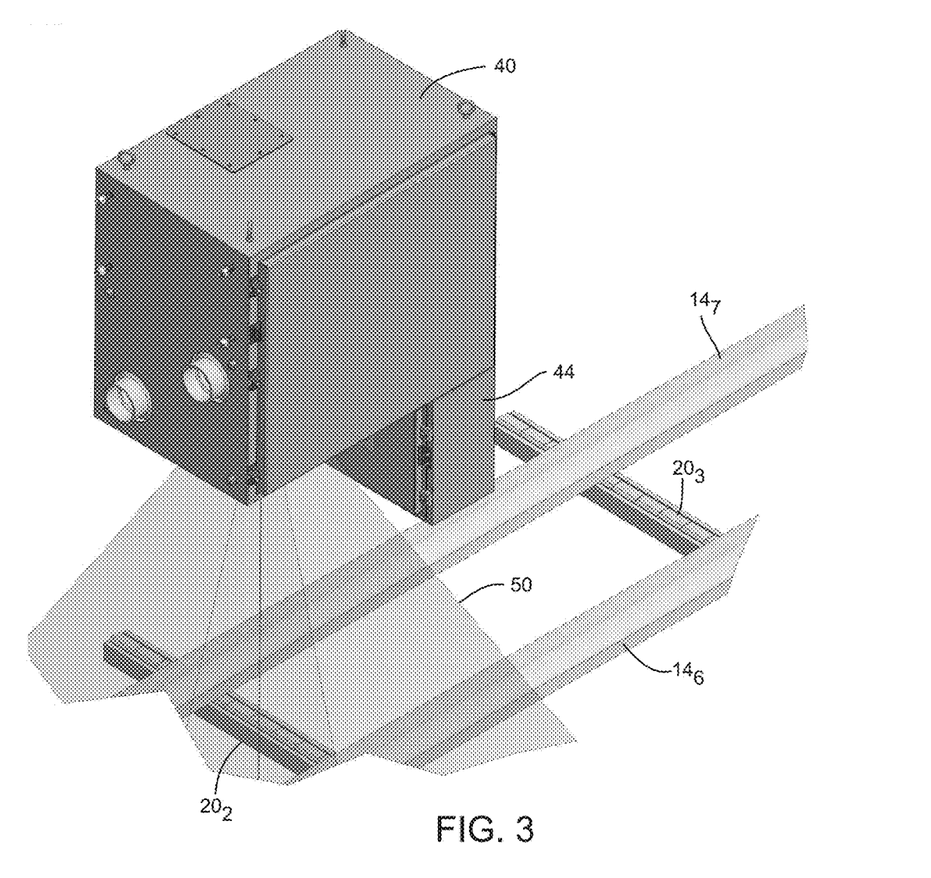
FIG. 3 is an enlarged fragmentary pictorial isometric view of enclosures for the image projector and 3D depth camera and of the field of view of the image projector shown in FIG. 1A.

An upright mounting member 30 supports at its top an L-shaped mounting arm 32 having a longer arm portion 34 extending along the lengths of lug chains 20 and a shorter arm portion 36 forming a right angle relative to arm portion 34 and extending in plane parallel relationship over boards 14 transported by conveyor 18. The free end of shorter arm portion 36 terminates in a mounting plate 38, to which is secured an enclosure 40 of an overhead image projector 42 (FIG. 2A). Enclosure 40 also houses a personal computer on which operate the image processing algorithms described below. An enclosure 44 of a three-dimensional depth camera ("3D depth camera") 46 (FIG. 2A) providing a depth image signal output to a board location tracking module 48 (FIG. 4) operating on the personal computer is affixed to enclosure 40 of image projector 42. Image projector 42 has a field of view 50, which, as shown in FIGS. 1A and 1B, covers about 7 ft. (2.13 m) down the length of boards $14_2$, $14_3$, $14_4$, $14_5$, $14_6$, and $14_7$ to project onto their surfaces images of one or more items of board attribute information, including grade symbols and trim symbols. The 3D depth camera 46 has a field of view 52. FIGS. 2A and 2B are diagrams showing, respectively, in the direction of board flow path 16 and in the viewing direction of check grader 12, the overlap of field of view 50 of image projector 42 and field of view 52 of 3D depth camera 46. With reference to FIGS. 2A and 2B, field of view 52 need not be the same size as that of field of view 50, but for practical reasons it is advantageous to have field of view 52 overlap field of view 50 as much as possible. FIG. 2A shows that field of view 52 spans farther in the direction transverse to board flow path 16 than does field of view 50. FIG. 2B shows that fields of view 50 and 52 span about the same distance in the direction of board flow path 16. FIG. 3 is an enlarged fragmentary view of enclosures 40 and 44 and field of view 50. The portion of conveyor 18 within field of view 50 is called a grading table.

Upright mounting member 30 supports along its length a mounting arm 60 from which suspends a board recognition system 62 positioned adjacent the upstream side of field of view 50. A preferred board recognition system 62 is a TrueQ® board tracking system manufactured by Lucidyne Technologies, Inc., which is the assignee of this patent application. The True-Q® system is disclosed in U.S. Pat. Nos. 7,426,422 and 7,200,458 and, as described below, implements a board recognition method that uses a previously acquired fiberprint of each board to confirm its identification upon reaching lug chains 20.

A closed loop air conditioner 64 mounted to upright mounting member 30 propels cold air flow at 4000-5000 BTU/hr through an insulated inlet duct 66 and an insulated outlet duct 68 connected to enclosure 40 to maintain an acceptable temperature environment for the electrical and electronic equipment operating inside of it. (FIGS. 2A and 2B show a version of air conditioner 64 that is mounted directly onto enclosure 40, thereby eliminating the ductwork shown in FIGS. 1A and 1B.)

Check grader 12 stands in a check grader work space 72 to visually inspect boards 14 as they are transported downstream from board recognition system 62 and pass through field of view 50. Check grader work space 72 is defined as an area located generally outside of field of view 50 and adjacent lug chain $20_1$ of the grading table. Check grader 12 standing in work space 72 performs one or both of two tasks. The first task is reading the board attribute information or symbols projected onto boards 14 on the grading table, and the second task is reaching into field of view 50 and manipulating or marking boards 14 on the grading table. FIGS. 1A and 1B show boards $14_2$, $14_3$, $14_4$, $14_5$, $14_6$, and $14_7$ lying on, board $14_8$ positioned upstream of, and board $14_1$ positioned downstream of, the grading table.

Figure 4:
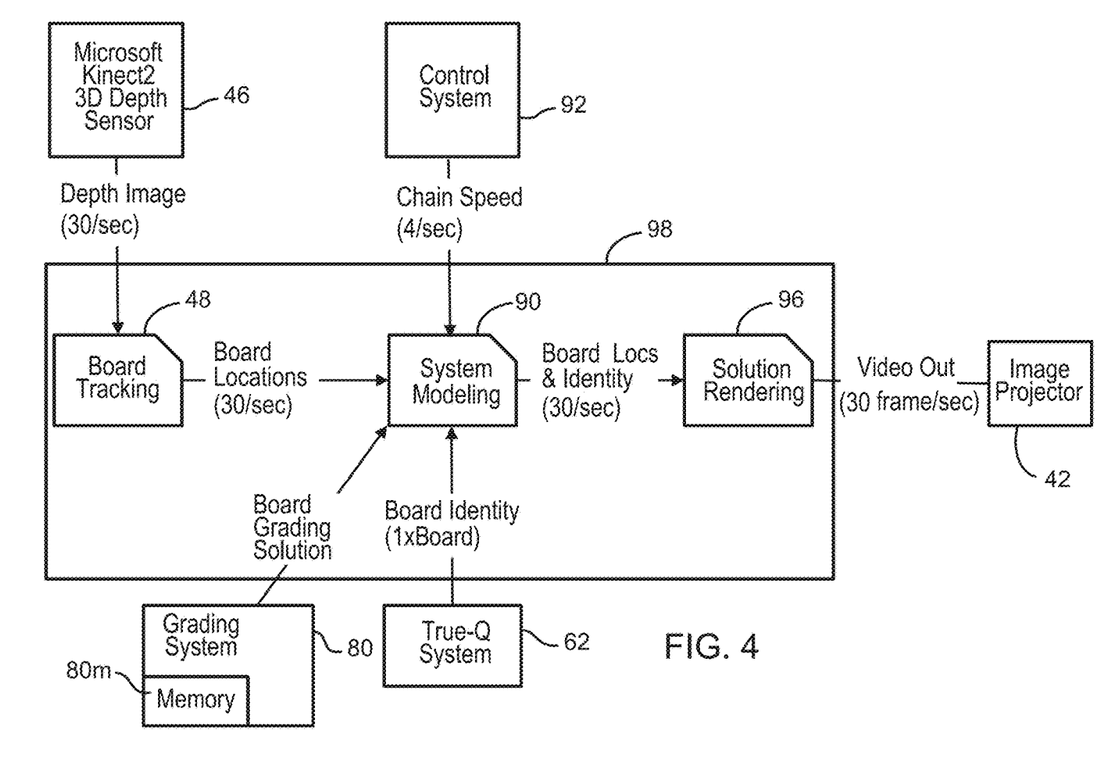
FIG. 4 is a block diagram of major sources of data and a personal computer contained in the image projector enclosure of the check grader-actuatable interface of FIGS. 1A and 1B.

FIG. 4 is a block diagram of the major sources of data and the information processing modules of check grader-actuatable interface 10. With reference to FIGS. 1A, 1B, and 4, before reaching board recognition system 62, boards 14 are scanned and assigned sequential board numbers that are used for all internal tracking and processing. A preferred board scanning and grading system 80 (FIG. 4) performing these operations is a GradeScan® automated lumber scanner, which is manufactured by Lucidyne Technologies, Inc. The GradeScan® automated lumber scanner is a linear scanner that scans boards 14 as they are conveyed end-to-end and pass through a scanning zone. Board scanning and grading system 80 uses sensor technologies to detect defects in and other attributes of (i.e., provide board feature quality information about) boards 14. Board scanning and grading system 80 captures images on all four sides of each one of boards 14 and associates the four images of the board with its sequential board number. These image data, board attribute information including grading designations representing board feature quality information, and the associated board number are stored in memory locations of a memory 80m. The GradeScan® board scanning and grading system 80 places no tracking symbols (e.g., ink, labels, and spray) on boards 14.

Boards 14 leaving board scanning and grading system 80 are transported by an endless conveyor (not shown) to lug chains 20. Boards 14 transported between board scanning and grading system 80 and lug chains 20 might become out of sequential order, or one of boards 14 might break and fail to reach lug chains 20. Board recognition system 62, which is positioned upstream of field of view 50, detects such re-ordering or absence of one of boards 14. Board recognition system 62 has a photoeye and an area camera, the photoeye detecting each one of incoming boards 14 and providing a trigger signal to which the area camera responds by capturing a single image of each one of boards 14 as they reach lug chains 20. Board recognition system 62 compares the single image with the images of the primary faces of the board captured by and stored in board scanning and grading system 80 to confirm the identity of the board before it enters field of view 50. If the single image does not match the expected board, board recognition system 62 looks upstream and downstream at images of several boards 14 previously measured by board scanning and grading system 80 in an attempt to find a match. Board recognition system 62 more heavily favors the closest boards 14.

Boards 14 leaving board recognition system 62 are transported into field of view 52 of 3D depth camera 46. A preferred three-dimensional depth camera is a Kinect2 sensor, manufactured by Microsoft® Corporation. The Kinect2 sensor is a physical device with depth sensing technology, a built-in color camera, an infrared (IR) emitter, and a microphone array, enabling it to sense the locations, movements, and voices of people. Board location tracking module 48 acquires at 30 frames/sec the depth image signal output of 3D depth camera 46.

FIGS. 5-1, 5-2, 5-3, and 5-4 are images developed by sequential processing of a depth image signal output of 3D depth camera 46.

Figure 51:
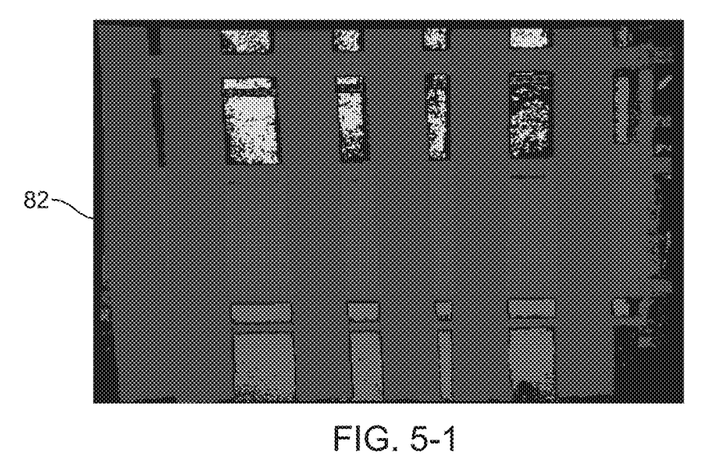

FIG. 5-1 shows a depth image acquired from 3D depth camera 46 by board location tracking module 48. Image 82 represents 6 ft.-8 ft. (1.83 m-2.44 m) of the ends of boards 14 nearer to check grader workspace 72.

Figure 52:
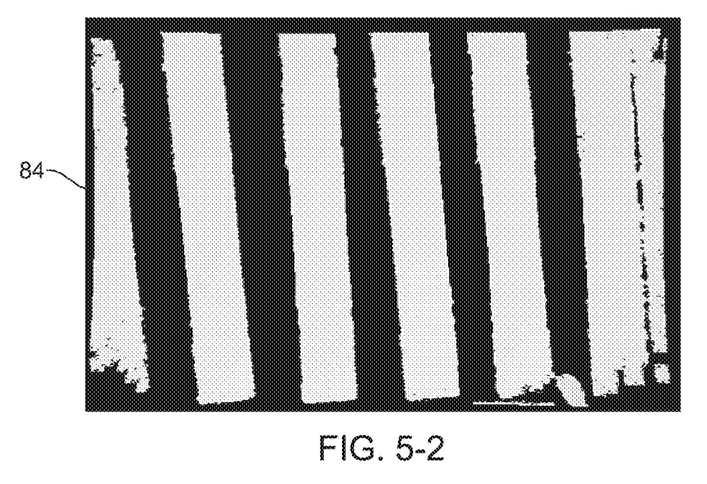

FIG. 5-2 shows a thresholded image 84 that is the result of application to image 82 of an image threshold algorithm masking all depth image information other than that of the top faces of boards 14. The image threshold algorithm can be any one of many well-known image threshold algorithms implemented in open source library software. The white regions of thresholded image 84 are categorized into blobs by application of software available from the Open Source Computer Vision (OpenCV) library of real-time computer vision programming functions. The blobs are filtered by size and shape; and blobs that are too small, wide, oblong, or excessively rotated in the plane of the board-carrying surface of conveyor 18 are discarded.

Figure 53:
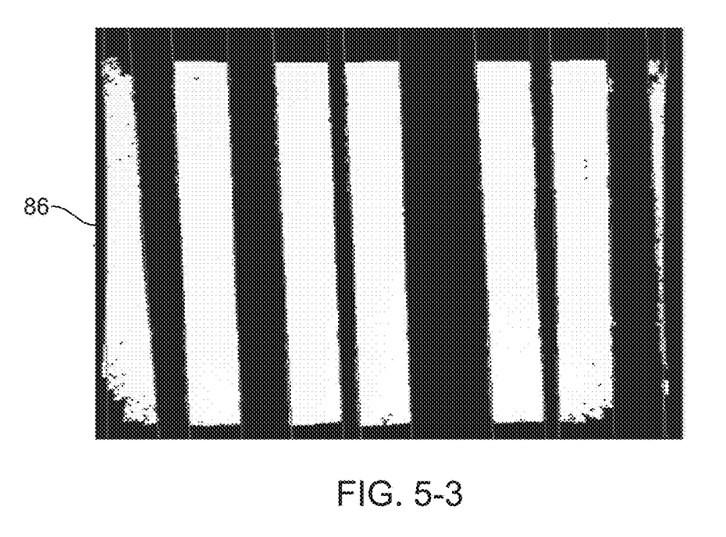

FIG. 5-3 shows an edge detected image 86 that is the result of vertical edge (both left and right) detection performed on the blobs. The vertical edges of each of the blobs are stored in a list of x, y coordinates.

Figure 54:
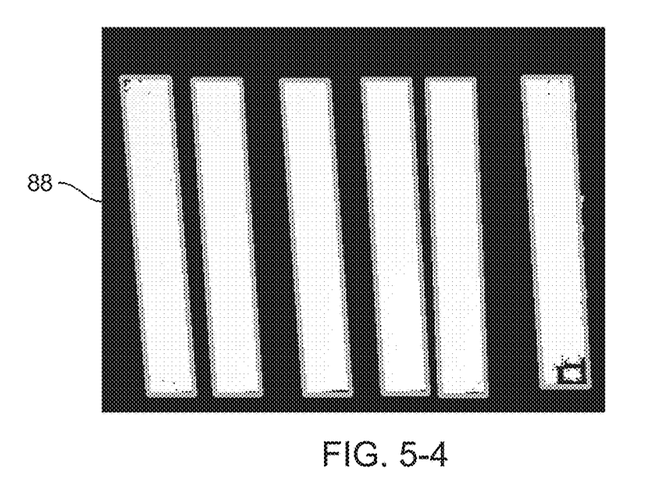

FIG. 5-4 shows a board blob location image 88 that is the result of applying to image 86 a random sample consensus (RANSAC) line-fitting algorithm or any one of many well-known line-fitting algorithms implemented in open source library software. A line fit is performed on the left and right edge points of each blob. The left and right lines fitted for each blob are compared for parallelism and separation distance to confirm that the blob has parallel left and right edges (as does a board) and that the edges are about the same width apart as that of boards 14. The remaining left/right line pairs and associated blob bounds are assumed to be boards 14. At this stage of image processing, the locations but not the identities of boards 14 are known.

With reference to FIG. 4, a system modeling module 90 receives from board recognition system 62 board identity information for each one of boards 14 and from board scanning and grading system 80 the board feature quality information or "solution" associated with each one of boards 14. The solution includes a set of board attribute information, such as lumber grade, species of lumber, moisture content, grading solution, trimming solution, strength, shape, thickness, width, and identification number. The location, identity, and solution set of each of boards 14 are grouped together in a list of virtual boards formed in system modeling module 90.

A programmable logic controller ("PLC") 92 controls the movement of lug chains 20 and includes an encoder 94 (FIG. 2B) that produces a board conveyor movement signal indicating the speed of lug chains 20.

The speed of lug chains 20 is read periodically (e.g., 4 times/sec) from PLC 92 by system modeling module 90. The location of lug chains 20 is derived by interpolation from the speed values read between 0.25 second intervals. This approach to measuring expected speed and location is called the chain movement model. System modeling module 90 uses the periodic readings of the location of lug chains 20 to periodically "move" forward in space the virtual boards represented in FIG. 5-4. System modeling module 90 uses the well-known Kalman filter algorithm to create a balance between measured speed of lug chains 20 transporting boards 14 and the measured locations of boards 14 by board location tracking module 48 so as to minimize lag and jitter. If 3D depth camera 46 detects no hand gestures of check grader 12 on the board, the Kalman filter weights favor the chain movement model to compute the location of the board. If 3D depth camera 46 detects a hand of check grader 12 on the board, system modeling module 90 is programmed to expect that check grader 12 is going to physically move the board in an unpredictable fashion. In this case, board location tracking module 48 is favored over the chain movement model to measure the location of the board. The detection of hand gestures is described in detail below. System modeling module 90 periodically, i.e., 30 times/sec, receives board blob locations from board location tracking module 48. System modeling module 90 compares the virtual boards in the list to the blob locations and pairs the virtual boards with the blob locations based on how close they are. System modeling module 90 then micro-adjusts the board locations and orientations to match what board location tracking module 48 is detecting. This operation of system modeling module 90 allows check grader 12 to displace boards 14 and thereby change their locations and angles, and the virtual board locations remain properly tracked with the actual boards 14.

As described above, each one of boards 14 enters the grading table, and board location tracking module 48 reads the location of that board. As the board moves down the grading table, board location tracking module 48 continuously tracks the location of that board (and all other previous boards 14). If check grader 12 reaches out and touches a specific one of boards 14, 3D depth camera 46 detects that interaction. (Check grader 12 touching a board essentially always displaces the board from its original orientation on lug chains 20.) Any inputs to interface 10 from the check grader 12 can now be associated with that board. These inputs could be, but are not limited to, additional hand gestures, to which 3D depth camera 46 is responsive; oral statements via microphone; or pressing of buttons on an input device.

With respect to detection of hand gestures of check grader 12, system modeling module 90 computes a high/low gesture zone and a left/right gesture zone. High/low gesture zone extends a fixed first distance, e.g., 2 ft. (0.61 m), along the length of a board from its end nearer to check grader workspace 72, and left/right gesture zone extends a fixed second distance, e.g., 6 in. (15.24 cm), along the width of the board in the direction of board flow path 16. System modeling module 90 establishes a reference depth by computing an average depth of the top surface of the board and average depths at the left- and right-hand sides of the board. This computation can be performed with use of any one of well-known algorithms.

Whenever 3D depth camera 46 detects a depth of the high/low gesture zone that differs from the reference depth, this condition indicates that a hand of check grader 12 has reached into that gesture zone. Since the depth of the gesture zone is known, system modeling module 90 can detect whether the hand of check grader 12 is in contact with or above the surface of the board.

Whenever 3D depth camera 46 detects a depth of the left/right gesture zone that differs from the average depths, this condition indicates that a hand of check grader 12 has been placed at the left-hand side of the board, if the depth of the left gesture zone has changed, or at the right-hand side of the board, if the depth of the right gesture zone has changed.

Establishing left/right and high/low gesture zones provides eight unique combinations of detectable gestures. These gestures made by check grader 12 include placing the left hand above or on the board surface, right hand above or on the board surface, left hand on the left-hand side of the board, right hand on the right-hand side of the board, left hand above the board surface and the right hand on the right-hand side of the board, and right hand above the board surface and the left hand on the left-hand side of the board.

System modeling module 90 is programmable to deliver to a solution rendering module 96 a complete set or a subset of the set of board attribute information in response to a specific gesture made by check grader 12. Board location tracking module 48, system modeling module 90, and solution rendering module 96 operate on processor circuitry of the personal computer contained in enclosure 40. A rectangular block 98 containing modules 48, 90, and 96 in FIG. 4 represents the personal computer.

Figure 6A:
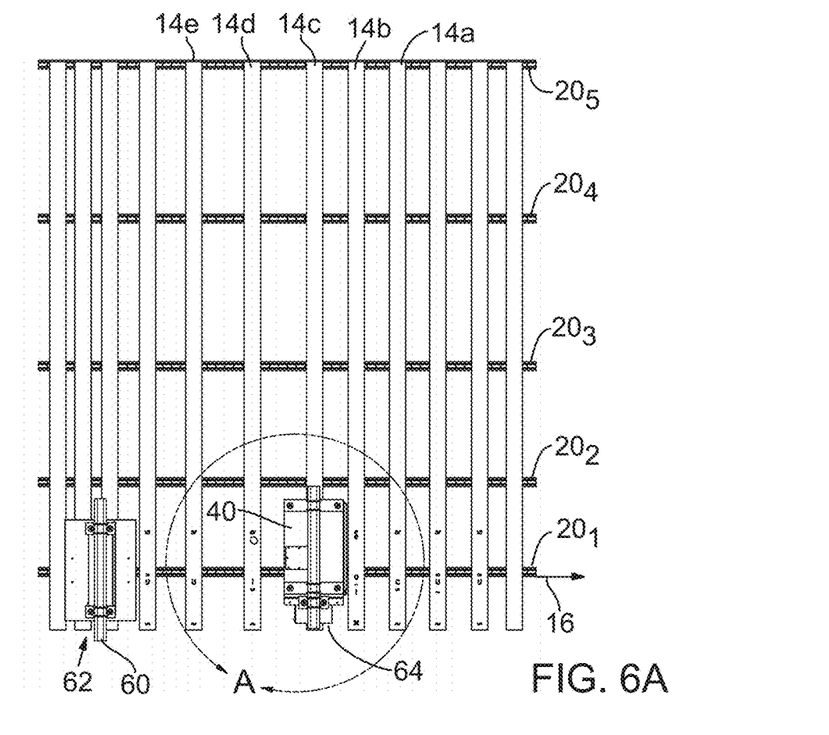
FIG. 6A is a diagram showing a top plan view of a group of twelve grade-quality measured boards transported along a board flow path.
Figure 6B:
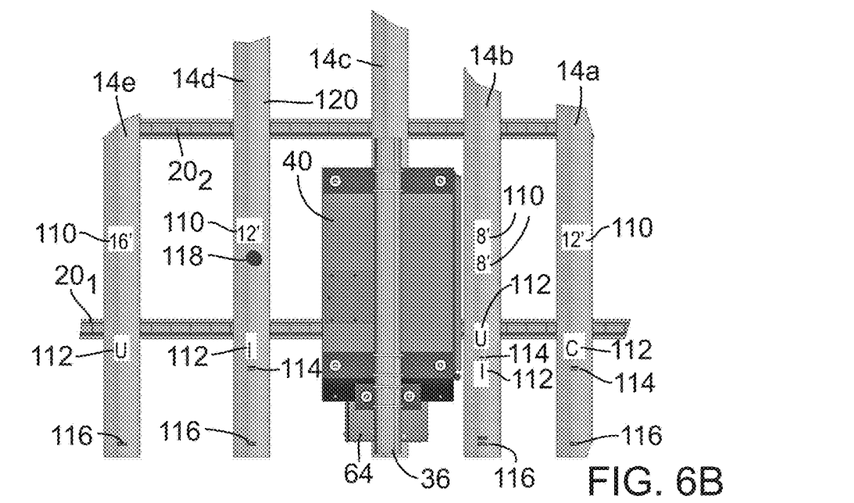
FIG. 6B is an enlarged fragmentary pictorial isometric view of five boards enclosed by a circle A drawn on FIG. 6A to identify a region within the field of view of the image projector and proximal to a check grader workspace.

For example, under nominal operating conditions, check grader 12 does not touch a board that check grader 12 concludes has the proper lumber grade projected onto the board surface. This nominal operating condition is illustrated in FIGS. 6A and 6B. FIG. 6A is a diagram showing a top plan view of a group of twelve grade-quality measured, generally parallel aligned boards 14 transported along board flow path 16. The three left-most and the one right-most boards 14 are outside of field of view 50 and, therefore, have no grade mark symbols or other board attribute information projected onto their top surfaces. FIG. 6B is an enlarged fragmentary view of boards 14a, 14b, 14c, 14d, and 14e enclosed by circle A drawn on FIG. 6A to identify a region within field of view 50 of image projector 42 and proximal to check grader workspace 72. Boards 14a, 14b, 14d, and 14e show projected on their top surfaces board length symbols 110, grade mark symbols 112, trim symbols 114, and board identification numbers 116. Board 14b shows two board length symbols 110 and two grade mark symbols 112 because board 14b is to be cut into two-8 ft lengths as indicated. Board 14d has a knot defect 118, and any board attribute information projected onto board 14c is obscured in FIGS. 6A and 6B by enclosure 40 and air conditioner 64.

Figure 7A:
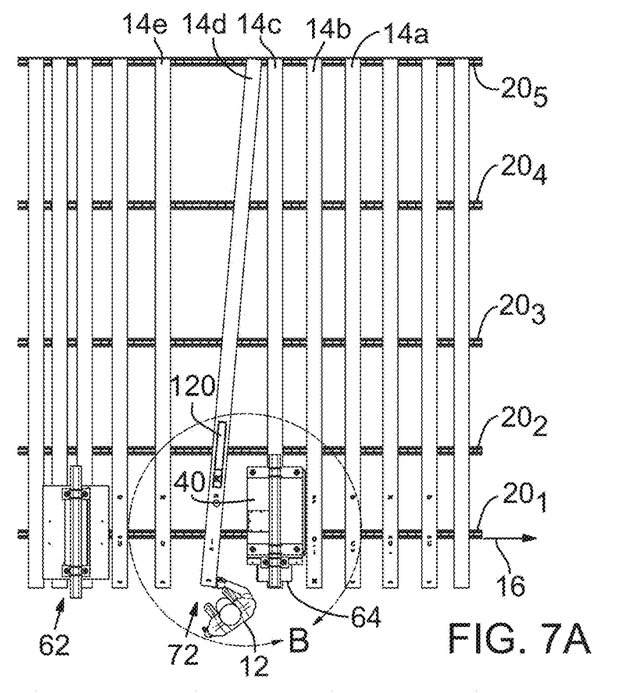
FIGS. 7A and 7B are reproductions of FIGS. 6A and 6B, respectively, with exception that FIGS. 7A and 7B show one of the five boards displaced from its original spatial alignment relative to adjacent boards.
Figure 7B:
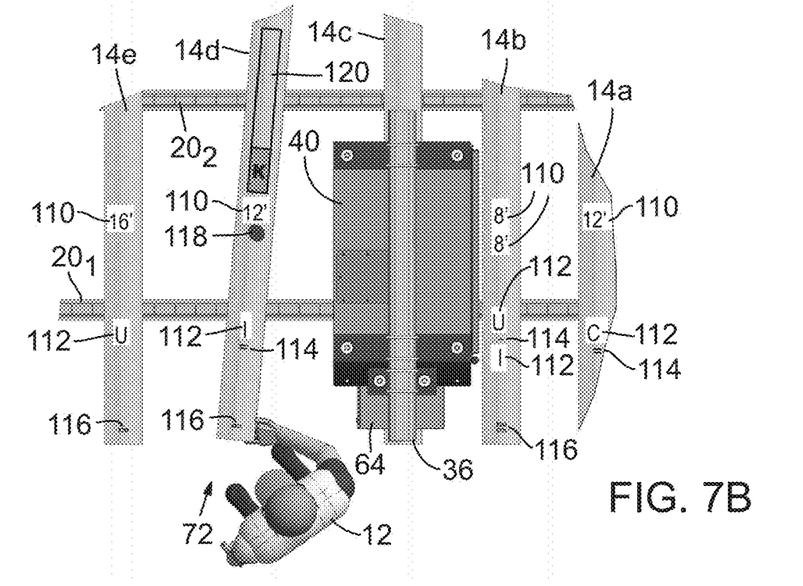

If upon inspection check grader 12 concludes that a board has projected on its surface board attribute information that was erroneously computed by board scanning and grading system 80, check grader 12 touches the surface of the board. The operating condition resulting from the touching of a board by check grader 12 is illustrated in FIGS. 7A and 7B. FIG. 7A differs from FIG. 6A in that a circle B replaces circle A of FIG. 6A to show check grader 12 moving board 14d and a consequent projection of additional board attribute information 120 onto the top surface of board 14d. FIGS. 7A and 6A are otherwise the same. FIG. 7B is an enlarged fragmentary view of boards 14a, 14b, 14c, 14d, and 14e and of check grader 12 enclosed by circle B.

The detection by board location tracking module 48 and system modeling module 90 of the hand of check grader 12 touching board 14d causes delivery to solution rendering module 96 board attribute information 120 that would be useful for check grader 12 to know. FIGS. 7A and 7B illustrate board attribute information 120 as an image of a rectangle representing a small scale rendering of board 14d, in which rectangle a smaller shaded area marked with "K" indicates a portion of board 14d spoiled by knot 118. Board 14d is shown displaced from its original generally parallel spatial alignment with adjacent boards 14e and 14c shown in FIGS. 6A and 6B. Board attribute information 120 is a member of a subset of board attribute information that is different from the subset of board attribute information shown in FIGS. 6A and 6B before the displacement of board 14d. The output of solution rendering module 96 is a 30 frames/sec stream of video, which is delivered to image projector 42. System modeling module 90 provides the different subset of solution information for projection onto the surface of the board. Board location tracking module 48 continuously monitors the location and orientation of each board; therefore, check grader 12 displacing board 14d to inspect it sees the projected information 110, 112, 114, 116, and 120 remain spatially aligned on the top surface of displaced board 14d as a consequence of the above-described adjustments made by system modeling module 90. This continuous monitoring enables check grader 12 to walk at a pace that permits observation of the projected information as lug chains 20 transport board 14d.

In the preferred embodiment described above, image projector 42 is the image display device that receives the set or subset of board attribute information from solution rendering module 96. First and second alternative image display devices include, respectively, a large format display screen and an augmented reality device. Each of the first and second alternative image display devices displays to an observer a rendering of a subset of the set of board attribute information in spatial alignment with renderings of images of virtual boards produced in accordance with the operation of board location tracking module 48 or captured by the color camera of 3D depth camera 46. The above-described operation of system modeling module 90 maintains spatial alignment between the rendering of board attribute information and renderings of images of a displaced selected grade-quality measured board transported on lug chains 20.

The use of virtual grades can improve board feature quality grading by facilitating reaction by check grader 12 to the grading output of board scanning and grading system 80. Lumber grades are determined by sizes and characteristics of defects in a board. To determine the grade of any one of boards 14, standard grade rules are applied to a board after it passes through the scanning zone of board scanning and grading system 80. If a board can satisfy the rules for more than one standard grade, board scanning and grading system 80 selects the standard grade associated with the maximum monetary value. Each of grade-measured boards 14 that are assigned a standard rule-based grade receives a grading association stamp and a location of a stack of similar feature quality boards 14 into which the board is to be placed. A board that is assigned a virtual grade has its own set of grading rules, but it is not assigned a grade stamp or a location. A virtual grade is expressed by a range of values that overlap values in two of the successive standard rule-based grades. The two successive standard rule-based grades represent higher and lower board feature qualities. These rules are stored in memory 80*m* of, and are applied by, board scanning and grading system 80.

Upon determination of an instance of a virtual grade condition, board scanning and grading system 80 activates and delivers to system modeling module 90 a board grading solution in the form of a virtual grade signal. To facilitate the reaction of check grader 12 to a board to which a virtual grade is assigned, system modeling module 90, in response to receipt of a virtual grade signal, causes delivery to solution rendering module 96 of virtual grade information in the form of a reduced set of operator-selected board attribute information for projection by image projector 52 onto the board. Reducing the amount of information shown on a board for which virtual grade consideration is presented suppresses distraction-inducing information clutter. Eliminating information clutter affords check grader 12 an opportunity to focus on the board feature or defect identified and to assign an appropriate rule-based grade. As the board travels through the grading table, the virtual grade information projected onto the board indicates that it has a virtual grade and should be inspected by check grader 12. If system modeling module 90 indicates that check grader 12 has taken no action, board scanning and grading system 80 reassigns to the board a standard rule-based grade that is associated with the virtual grade. If system modeling module 90 indicates that check grader 12 has interacted with the board, check grader 12 can assign a different standard rule-based grade to the board. After passing check grader 12, the board receives an appropriate grade stamp and location, either the rule-based grade stamp associated with the virtual grade or a new standard rule-based grade assigned by check grader 12.

An alternative use of virtual grades entails specifying first and second virtual grades for application to boards passing through the scanning zone. The first virtual grade is expressed by a first range of values that overlap values in a first pair of the successive standard rule-based grades representing first higher and first lower board feature qualities. The second virtual grade is expressed by a second range of values that overlap values in a second pair of the successive standard rule-based grades representing second higher and second lower board feature qualities. The second lower board feature quality is of lesser board feature quality than the first lower board feature quality. A typical implementation of this alternative use is one in which one of the standard rule-based grades is common to the first virtual grade and the second virtual grade. Check grader 12 is alerted to assess whether a board exhibits board feature quality that exceeds one of the first and second lower board feature qualities.

The following example demonstrates the relationship between standard rule-based grades and virtual grades.

EXAMPLE

This example defines three standard rule-based grades (N1, N2, and N3) and two virtual grades (V1 and V2) and uses knot diameter as the grade discriminator. (Any type of defect can be used as a grade discriminator.) The rule for maximum knot diameter increases in the following grade order: N1, V1, N2, V2. Monetary value of a board on which a knot appears decreases in the same order, with grade N3 being last. Since it is the lowest possible grade, N3 has no maximum knot diameter rule. All knots pass grade N3. Grade V1 is associated with grade N2, and grade V2 is associated with grade N3.

Figure 8:
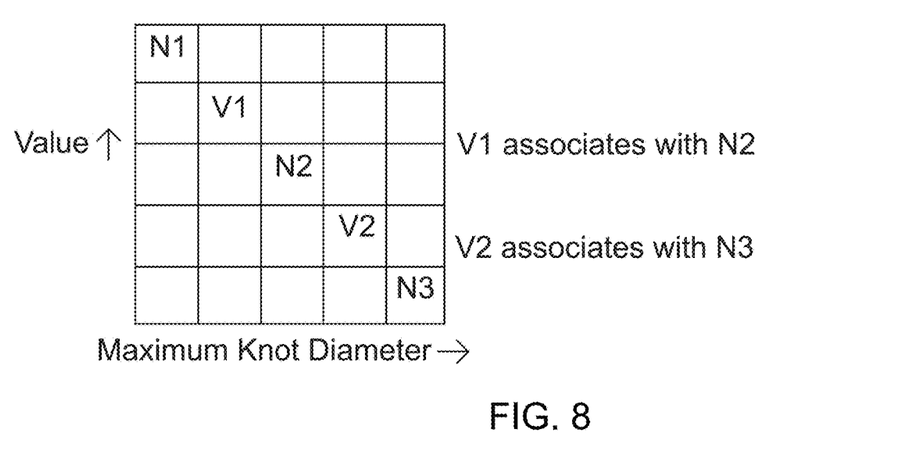
FIG. 8 is a diagram showing the relationship between the diameter of a knot appearing in a board and the monetary value of the board.

The grade V1 rules are the same as the grade N2 rules, except the maximum knot diameter is lower. The grade V2 rules are the same as the grade N3 rules, except grade V2 has a rule for maximum knot diameter that is larger than the knot diameter in the equivalent rule in grade N2. These rules are stored in memory 80*m*. FIG. 8 is a diagram showing the relationship between the diameter of a knot appearing in a board and its monetary value.

Whenever a board to which grade N3 is assigned passes check grader 12, no virtual grade signal has been activated and no virtual grade information is present. Check grader 12 lets the board pass by without touching it. This board receives the N3 grade stamp and later arrives at the N3 grade board lumber storage location.

Whenever a grade V2 board passes check grader 12, an activated virtual grade signal causes projection of virtual grade information onto the board, which check grader 12 inspects. This board satisfies both grades V2 and N3, but grade V2 is of greater monetary value. If check grader 12 takes no action, the final grade will be grade N3. Check grader 12 will, however, inspect the largest knot on the board. If the board can justifiably be assigned the N2 grade, check grader 12 will assign and mark the board as grade N2 and thereby avoid value loss resulting from assignment of a wrong grade.

The same reasoning can apply for assessing defects that are more subjective, such as knot quality. Check grader 12 inspects the largest unsound knot and directs the board to the appropriate grade.

The case may be that the quality of a knot technically fails the N2 grade, but, in combination with other less severe defects on the board, it can still be judged to be a grade N2. Check grader 12 marks that board to upgrade it to grade N2.

The case may also be that a stain covers the edge of a knot such that board scanning and grading system 80 incorrectly reads it as a borderline knot, but the knot in fact is just larger than a legitimate grade N2 knot. In this case, check grader 12 takes no action and the board becomes grade N3, instead of below grade N2.

The practice of virtual grade marking reduces above-grade errors, which result in setting board lumber at monetary values that are less than what the board lumber is worth, and below-grade errors, which result in setting board lumber monetary values that are greater than what the board lumber is worth.

Board grade designation is attained from the point of view of check grader 12. If the board grading system is assembling a package of Grade #2 boards and check grader 12 finds a Grade #1 board in the pack, that board is deemed to be above grade. The lumber mill selling the lumber would be shortchanged as a result of the above-grade board designation because the price for a Grade #2 board is less than the price of a Grade #1 board. If the board grading system is assembling a package of Grade #1 boards and check grader 12 finds a Grade #2 board in the pack, that board is deemed to be below grade. A customer buying the lumber would be overcharged as a result of the below-grade designation because the customer would be paying a Grade #1 price for the lower price Grade #2 board.

Most automatic grading systems perform satisfactorily detecting below-grade boards and staying within an error budget of 5%. If the below-grade error is above 5%, check grader 12 puts a hold on lumber shipments. Holding lumber shipments is very expensive for the lumber mill. Check grader 12 might inform the lumber mill operator of the number of above-grade boards; but even if the number of above-grade boards is greater than 5%, the lumber can be shipped to customers.

Since the price difference between Grade #2 lumber and Grade #3 lumber is very large, above-grade error in Grade #3 lumber is expensive. Virtual grades can help lumber mill operators realize revenue that would have been lost to above-grade error.

The use of virtual grades can be implemented in several ways, two of which are described below.

A rudimentary implementation entails use of a paint sprayer marking a board in response to activation of a virtual grade signal by board scanning and grading system 80. Check grader 12 inspecting a board marked with a spray-painted "V" assesses which standard rule-based grade should be applied and marks the board accordingly.

A more automated implementation reduces the amount of board attribute information image projector 52 projects onto boards 14. System modeling module 90 is typically configured by lumber mill operators to cause solution rendering module 96 to produce only virtual grade information symbols for projection by image projector 52 onto boards 14. No information is projected onto boards 14 to which no virtual grade is assigned.

An operator can adjust the number of virtual grade defects relative to the number of associated standard rule-based grade defects to set an appropriate number of virtual grade information-assigned boards 14 presented to check grader 12. Operators who adjust the virtual grade rules typically limit to 15%-20% the number of boards 14 onto which information is projected. Such limitation of projected information allows check graders 12 to find above-grade boards 14 without needless distraction.

To keep relatively constant the amount of time allotted to check grader 12 to assess a board to which a virtual grade is assigned, the operator can compensate for a faster conveyor speed by setting to a lower value the number of virtual grades that image projector 52 would project onto boards 14.

In either implementation, after check grader 12 has applied the appropriate standard rule-based grade mark to the board, a grade mark reader positioned downstream of the grading table reads the grade mark and causes a sorter control system to direct the board to a corresponding board lumber storage location.

It will be obvious to those having skill in the art that many changes may be made to the details of the above-described embodiments without departing from the underlying principles of the invention. The scope of the present invention should, therefore, be determined only by the following claims.

The invention claimed is:

1. A method of improving board feature quality grading by facilitating human check grader reaction to grading output produced by an automatic grading system included in a board lumber scanning system, the board lumber scanning system scanning faces of boards that pass through a scanning zone and projecting onto the boards grading designations that represent board feature quality information produced after analysis of the boards by the automatic grading system, the grading designations developed from successive standard rule-based grades representing board structure and appearance metrics, each of the standard rule-based grades expressed as a range of values, and the ranges of values of successive standard rule-based grades representing different degrees of board feature qualities, comprising:
    specifying, for application by the automatic grading system to the faces of boards passing through the scanning zone, a virtual grade stored in memory and expressed by a range of values that overlap values in a pair of the successive standard rule-based grades, the pair of successive standard rule-based grades representing higher and lower board feature qualities;
    producing, by the board lumber scanning system, a board grading solution in response to detection of a board feature quality representing the virtual grade of a board analyzed by the automatic grading system;
    in response to the board grading solution, projecting a virtual grading designation onto the board to which the virtual grade corresponds and to which a check grader can react to assess whether the board exhibits board feature quality that exceeds the lower board feature quality of the pair of successive standard rule-based grades;
    processing check grader input to a check grader-actuatable interface of the board lumber scanning system, the check grader input indicating the check grader's assessment made in reaction to the virtual grading designation; and
    assigning to the board, by the automatic grading system, the standard rule-based grade representing the higher board feature quality in response to receipt of the check grader input indicating an assessment justifying the higher board feature quality in reaction to the virtual grade designation.

2. The method of claim 1, further comprising not projecting grading designations of the successive standard rule-based grades onto at least some of the boards onto which no virtual grade is indicated to suppress distraction-inducing information clutter and thereby allow the check grader to concentrate on assessing the board feature quality of the board onto which a virtual grade designation is indicated.

3. The method of claim 1, in which the indicating a virtual grading designation includes projecting the virtual grading designation onto the board.

4. The method of claim 1, in which the indicating a virtual grading designation includes application of a physical mark onto the board.

5. The method of claim 1, in which the virtual grade constitutes a first virtual grade expressed by a first range of values that overlap values in a first pair of the successive standard rule-based grades representing first higher and first lower board feature qualities;
    further comprising specifying, for application by the automatic grading system to the faces of boards passing through the scanning zone, a second virtual grade expressed by a second range of values that overlap values in a second pair of the successive standard rule-based grades representing second higher and second lower board feature qualities, the second lower board feature quality being of lesser board feature quality than the first lower board feature quality; and
    in which the check grader, in reaction to the virtual grading designation, assesses whether the board exhibits board feature quality that exceeds one of the first and second lower board feature qualities.

6. The method of claim 5, in which one of the standard rule-based grades is common to the first virtual grade and the second virtual grade.

7. The method of claim 1, in which the check grader input includes a hand gesture by the check grader.

8. The method of claim 7, in which the check grader's hand gesture includes physical contact with the board.

9. The method of claim 1, in which the check grader input includes oral statements made by the check grader.

10. The method of claim 1, in which the check grader input includes actuating, by the check grader, control buttons on an input device.

\* \* \* \* \*